(12) United States Patent
Foley et al.

(10) Patent No.: US 8,782,543 B2
(45) Date of Patent: Jul. 15, 2014

(54) PRODUCT OPTIONS CALCULATOR FOR A BLOOD PROCESSING SYSTEM

(75) Inventors: John T. Foley, Wheeling, IL (US); Jonathan Prendergast, Chicago, IL (US); Jennifer A. Hollenstein, Grayslake, IL (US); Timothy A. Johnson, Issaquah, WA (US)

(73) Assignee: Fenwal, Inc., Lake Zurich, IL (US)

(*) Notice: Subject to any disclaimer, the term of this patent is extended or adjusted under 35 U.S.C. 154(b) by 402 days.

(21) Appl. No.: 12/393,802

(22) Filed: Feb. 26, 2009

(65) Prior Publication Data

US 2009/0217202 A1 Aug. 27, 2009

Related U.S. Application Data

(60) Provisional application No. 61/031,947, filed on Feb. 27, 2008.

(51) Int. Cl.
*G06F 3/048* (2013.01)
*G06F 3/00* (2006.01)
*A61M 1/36* (2006.01)
*G06F 19/00* (2011.01)
*A61M 1/38* (2006.01)

(52) U.S. Cl.
CPC ...... *G06F 19/3406* (2013.01); *A61M 2205/502* (2013.01); *A61M 2205/52* (2013.01); *G06F 3/048* (2013.01); *A61M 1/38* (2013.01); *A61M 1/3693* (2013.01)
USPC .................................. 715/764; 705/2; 705/3

(58) Field of Classification Search
USPC .................................. 715/810, 764; 705/2, 3
See application file for complete search history.

(56) References Cited

U.S. PATENT DOCUMENTS

| 7,072,769 | B2 | 7/2006 | Fletcher-Haynes et al. | |
|---|---|---|---|---|
| 7,354,415 | B2 | 4/2008 | Bainbridge et al. | |
| 7,430,478 | B2 | 9/2008 | Fletcher-Haynes et al. | |
| 2003/0154108 | A1* | 8/2003 | Fletcher-Haynes et al. | 705/3 |
| 2004/0088189 | A1* | 5/2004 | Veome et al. | 705/2 |
| 2005/0209883 | A1* | 9/2005 | Fletcher-Haynes et al. | 705/2 |
| 2006/0058900 | A1* | 3/2006 | Johanson et al. | 700/83 |

* cited by examiner

*Primary Examiner* — Ryan Pitaro
*Assistant Examiner* — Tuan S Nguyen
(74) *Attorney, Agent, or Firm* — Hanley, Flight & Zimmerman, LLC

(57) ABSTRACT

Systems, methods, and computer readable media are provided for product options calculation with respect to an apheresis instrument. An example product options calculator system for an apheresis instrument includes a preset information module including preset information regarding blood component products and configuration information. The system also includes a donor specific input module receiving donor specific information about a blood donor from a user. The system further includes a blood product options calculator calculating available blood component collection procedure options and associated settings within the constraints of the preset information and the donor specific information from which a user can choose to configure the apheresis instrument. Additionally, the system includes a display for displaying available component collection options to the user with respect to the apheresis instrument. The system also includes an interface accepting user input.

21 Claims, 11 Drawing Sheets

PRODUCT OPTIONS CALCULATOR FOR A BLOOD PROCESSING SYSTEM

CROSS-REFERENCE TO RELATED APPLICATIONS

The present application claims the benefit of priority to U.S. Provisional Patent Application No. 61/031,947, filed on Feb. 27, 2008, entitled "PRODUCT OPTIONS CALCULATOR FOR A BLOOD PROCESSING SYSTEM", which is herein incorporated by reference in its entirety.

FIELD OF THE INVENTION

The present invention relates generally to methods and apparatus for collecting a blood component, and more particularly, to methods and apparatus for determining all available options for collecting a blood component prior to the collection procedure.

BACKGROUND OF THE INVENTION

An apheresis instrument is used to separate blood components from whole blood. Such apheresis instruments are commercially available from various sources, including the Amicus® instrument and the ALYX™ blood processing system which are available from Fenwal Inc. of Lake Zurich, Ill. Such instruments, also known as "separators", typically separate a selected blood component from whole blood by passing the blood of a donor through the instrument to separate one or more blood components from the whole blood. The remainder of the whole blood is then returned to the circulatory system of the donor. It is, therefore, an extracorporeal blood component collection process.

The Amicus instrument utilizes a centrifuge to separate blood components. A disposable apheresis kit is connected to the Amicus instrument for collection of the desired blood component. The instrument has pumps, clamps, and valves that move and direct donor blood through the kit. Part of the kit includes a bag into which the desired blood component is collected. Most of the remainder of the kit is disposable after completion of the collection process. Such kits are often referred to as "disposables".

As background, the Amicus instrument has had a platelet yield estimator. The operator of the Amicus device can decide to collect plasma and/or red blood cells (RBC) in addition to platelets. The operator enters information concerning the donor, such as platelet precount, mean platelet volume, donor weight, donor height, donor hematocrit and gender. If no information is entered for any one of these factors, a default value is used. The operator also enters the desired platelet yield, such as a single dose, a double dose or a triple dose collection. The platelet yield estimator then estimates the whole blood to process, platelet post count, post hematocrit, and the subsequent amount of time required for a blood product collection procedure, including for collection of multiple platelet products. If the time required for the entered procedure, platelet post count, post hematocrit, or the whole blood to process is outside a desired limit, the operator will revise the targeted products to be collected until the procedure time, platelet post count, post hematocrit, or whole blood to process falls within the acceptable limit.

However, the efficiency of the blood collection process can be enhanced if the operator of the apheresis instrument could select the type of blood component to be collected from a display or listing of all potentially available collection choices.

SUMMARY OF THE INVENTION

Certain examples provide systems, methods, computer program products, and apparatus for calculating available blood product options for a donor using a blood processing system.

Certain examples provide a product options calculator system for an apheresis instrument. The product options calculator system includes a preset information module including preset information regarding blood component products and configuration information. The system also includes a donor specific input module receiving donor specific information about a blood donor from a user. The system further includes a blood product options calculator calculating one or more available blood component collection procedure options, the options including at least one platelet collection procedure, and associated settings within the constraints of the preset information and the donor specific information from which a user can choose to configure the apheresis instrument. Additionally, the system includes a display for displaying available component collection options to the user with respect to the apheresis instrument and an interface accepting user input.

Certain examples provide a method for calculating all of the blood component collection options for a specific donor. The method includes storing preset information regarding blood component products and apheresis configuration information. The method also includes receiving donor specific information about a donor. The method further includes calculating one or more available blood component collection procedure options and associated settings within the constraints of the preset information and the donor specific information from which a user can choose to configure the apheresis instrument, the options including at least one platelet collection procedure. Additionally, the method includes displaying the available blood component collection options for user review and selection to configure a blood processing system.

Certain examples provide a computer readable medium having a set of instructions for execution on a computing device, the set of instructions providing a blood product options calculator system when executed. The set of instructions includes a preset information module including preset information regarding blood component products and configuration information. The set of instructions also includes a donor specific input module receiving donor specific information about a blood donor from a user. The set of instructions further includes a blood product options calculator calculating one or more available blood component collection procedure options, the options including at least one platelet collection procedure, and associated settings within the constraints of the preset information and the donor specific information from which a user can choose to configure the apheresis instrument. The set of instructions additionally includes a display for displaying available component collection options to the user with respect to the apheresis instrument. The set of instructions includes an interface accepting user input.

BRIEF DESCRIPTION OF THE DRAWINGS

Certain example embodiments of the invention, together with features and the advantages thereof, may best be understood by reference to the following description taken in conjunction with the accompanying drawings, in which like reference numerals identify like elements in the figures, and in which.

Figure 1:
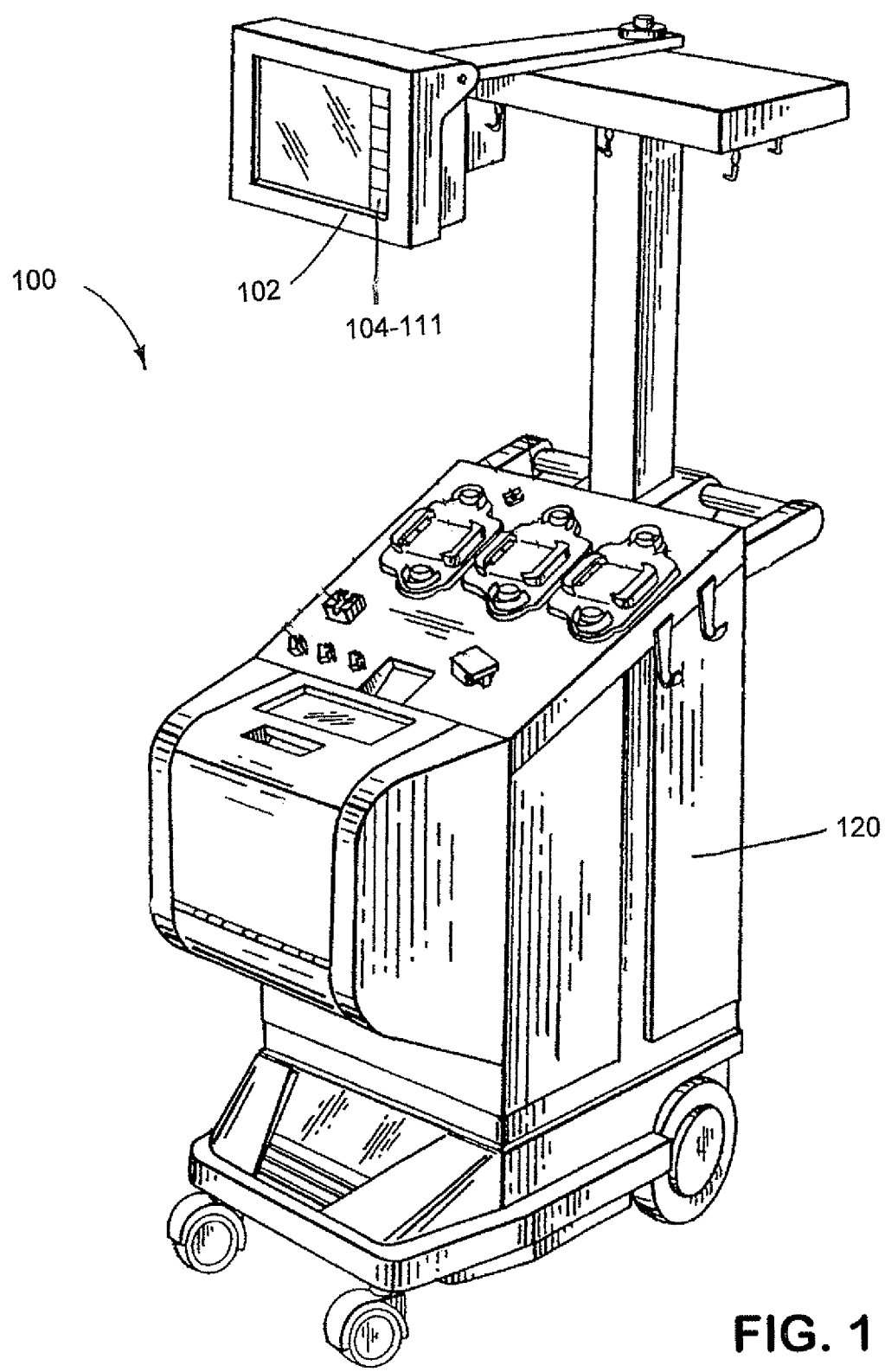
FIG. 1 is a perspective view of a blood processing system with an internal product options calculator.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DESCRIPTION OF CERTAIN EMBODIMENTS

It will be understood that the present invention may be embodied in other specific forms without departing from the spirit thereof. The present examples and embodiments, therefore, are to be considered in all respects as illustrative and not restrictive, and the invention is not to be limited to the details presented herein.

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

In certain examples, options, such as user-specified options regarding a donor and/or available equipment, can be generated to provide an operator with available options and associated settings from which to choose to configure a blood processing system to obtain blood product(s) from a donor. For example, from a set of twelve total soft good or blood product options available on a blood processing/collection system (e.g., single, double, or triple platelet products; with or without plasma; with or without red blood cells; etc.), a subset of applicable blood product collection options can be determined.

FIG. 1 illustrates a blood processing system 100, such as the AMICUS™ system commercially available from Fenwal, Inc., for the collection of a blood product. System 100 includes a display 102 and an internal product options calculator 120. For example, product options calculator 120 can include a digital processor, such as a microprocessor, microcontroller, or the like.

Display 102 can include touch sensitive fields 104-111 for entering default information for the selection of blood component collection information, for example. The settings entered by the touch sensitive fields 104-111 can also be designated as "preselects". These preselects can establish information to be used by the product options calculator in the event that specific information about the donor is not entered prior to a collection procedure. Alternatively and/or in addition, instrument 100 can include one or more input devices for entering default information, such as a keyboard, one or more switches (not shown), one or more buttons (not shown), and/or the like.

In certain examples, a set of default parameters can be set up by a user, such as an operator or administrator. Default parameters can be established for single needle procedures, double needle procedures, and/or common defaults for both single and double needle procedures, for example. A platelet yield estimator operating in conjunction with a blood processing system, such as the blood processing system 100, can also have a set of defaults associated with its operation. Using the platelet yield estimator, a whole blood to process can be calculated given a desired yield and applicable parameters. Alternatively, given a desired whole blood to process and applicable parameters, an estimated yield can be calculated.

A product options calculator takes the parameter information, estimated yield, etc., and calculates available blood product procedures that do not violate certain preset collection rules, such as industry standards, FDA clearance, etc., based on the parameter information. In certain examples, based on parameter inputs and changes made by a user to those parameter inputs, alarms (e.g., visual messages or indicators displayed to inform and alert a user via a user interface and display screen) can be generated when parameter settings violate one or more rules for blood product procedures. In certain examples, no priority is given to blood product procedures in a list of available procedures for selection. In certain examples, the blood processing system must collect a platelet product with each procedure.

In certain examples, a product options calculator permits a collection center to enter a number of preferences, preselects, or "presets" in accordance with its desires or needs. For example, these presets may include:

1. Desired red blood cell type (A, B, AB, O, positive, negative)
2. Desired plasma type (A, B, AB, O, positive, negative)
3. Extra-corporeal volume limit
4. Minimum acceptable pre-count—double platelet product
5. Minimum acceptable pre-count—triple platelet product
6. Number of platelets that define a single ($3\times10^{11}$ or $4\times10^{11}$) collection
7. Number of platelets defining a double collection or number of platelets defining a triple collection
8. Maximum procedure time These presets can be revised from time to time as the collection center's needs or parameters change.

In addition, for each donor, a series of individual data or factors are entered into a platelet yield estimator. This information may include:
1. Platelet pre-count
2. Mean platelet volume
3. Donor weight
4. Donor height
5. Donor hematocrit
6. Gender (male/female)
7. Blood type
8. Frequency of donation (e.g., frequent, infrequent, etc.)

The platelet yield estimator uses these factors, including any default information, to estimate a length of time that any selectable collection procedure will involve. Nomograms can be used by the estimator in its determinations. As examples, a single platelet collection may be estimated to involve 39 minutes, a single platelet plus plasma collection may be estimated to involve 42 minutes, a double platelet collection may be estimated to involve 73 minutes, etc.

As further examples, a maximum red cell volume (e.g., 0 to 200) can be set by an operator to eliminate or include some or all red blood cell procedures. A selection of a double needle procedure can eliminate all red blood cell procedures, for example. A selection of a female donor can be configured to eliminate all plasma procedures in the default settings, for example.

The product options calculator then compares the various collection options to the presets to determine which blood product collection options comply with the presets entered by the blood collection center. Potential collection options are accepted or rejected depending on how the collection options compare to the presets. Blood product collection options can be eliminated for a donor based on one or more limits, times, pre-counts, target yields, plasma product volume, etc. For example, if the maximum collection time is preset at 60 minutes and the estimated time to collect a double platelet dose is 73 minutes, the double platelet option will be excluded from the collection options. Product options can then be narrowed based on donor plasma type and blood type. For example, if the presets include only Type B and Type O blood for the collection of a red blood cell (RBC) product, red blood cells will be excluded as one of the collection options for a donor with Type A blood. As another example, total plasma collection limits can be specified to limit total plasma collection to 600 milliliters for a donor weighing less than 175 pounds and 700 milliliters for a donor weighing greater than or equal to 175 pounds. The estimator/calculator can determine what portion is plasma and what portion is acid-citrate-dextrose storage solution, for example.

In certain examples, the product options calculator accepts a donor blood type and frequency of donation (e.g., frequently or infrequently). The remainder of the parameter information can be transferred from the platelet yield estimator. In certain examples, a user change of parameter information in the product options calculator will change corresponding parameter information in the platelet yield estimator as well.

Those collection options that meet the preset requirements are then presented on a screen, including the estimated procedure time for each collection option. That is, all of the collection options that a particular donor is capable of providing, which are not excluded by the previously entered presets, are listed on the screen. The operator then manually selects the desired collection option.

A user can select an available procedure option from the product options calculator, and, upon returning to the estimator, find that the estimator has been populated with information and/or other settings for the selected product. In certain examples, alerts are displayed on the user interface screen if settings and/or user changes to those settings violate a rule. In certain examples, a help tab or user interface option provides information to the user indicating why other product collection options are unavailable.

After selecting a procedure, parameter values can be modified in the platelet yield estimator if desired for the procedure. For example, as discussed above, whole blood to process and yield can be an input or an output and other parameter values will adjust based on those values and the platelet yield estimator. For example, if a user enters a yield, the system calculates whole blood to process, estimated acid-citrate-dextrose solution volume, post-hematocrit, collection time, volume to storage platelet product, etc. As discussed above, a user change of parameter information in the platelet yield estimator will change corresponding parameter information in the product options calculator In all of the calculations, comparisons can be performed by software associated with the options calculator. This software resides in the blood component collection instrument, for example. Every procedure starts with the default values for each factor used by the platelet yield estimator until an operator at the blood collection center manually enters information about the new donor. In certain examples, a user can access configuration parameters, change parameters, and select different options to reprogram the blood processing system at any time, even during collection. In certain examples, the user is not locked into a particular option chosen but can modify parameters unless the modification violates a rule, as discussed above.

In certain examples, no information is stored or kept from procedure to procedure for use in a subsequent procedure. However, the presets previously entered by the blood collection center may remain the same for subsequent procedures.

Figure 2:
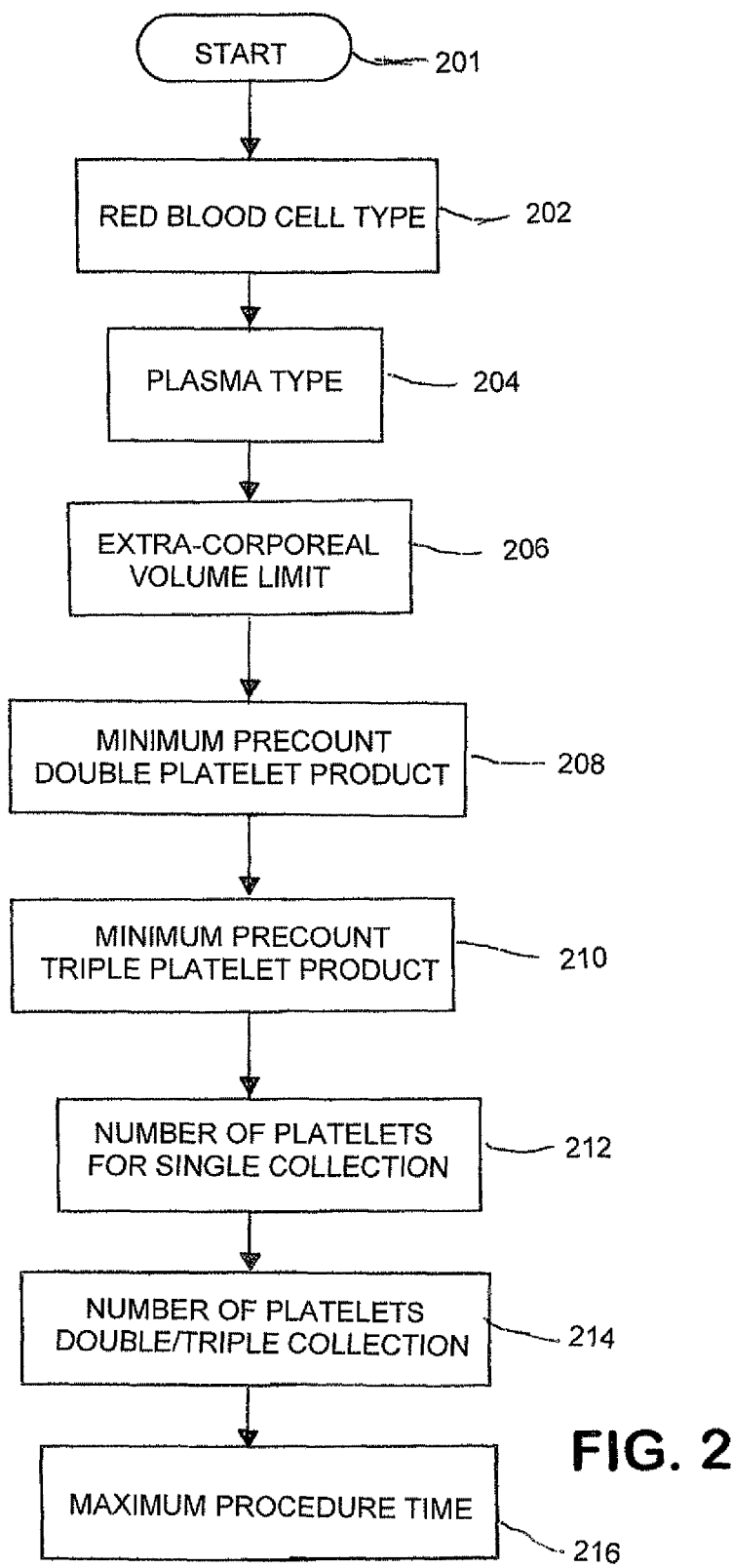
FIG. 2 is a flow chart of the preselects for the product options calculator which may be set prior to a blood component collection process.

FIG. 2 is a flow chart, generally designated 200, of preselects for the product options calculator 120 that can be set prior to a blood component collection process. The process of setting the preselects, such as by entering information on touch sensitive fields 104-111 in FIG. 1, begins with initiating the start bubble 201. At block 202, a desired red blood cell type (A, B, AB, O, positive, negative) can be entered, such as on touch sensitive field 104. At block 204, a desired plasma type can be entered, such as on touch sensitive field 105. At block 206, an extra-corporeal volume limit can be entered, such as on touch sensitive field 106. A minimum acceptable pre-count for a double platelet product is entered at block 208, such as on touch sensitive field 107. Similarly, a minimum acceptable pre-count for a triple platelet product is entered at block 210, such as on touch sensitive field 108. A number of platelets that define a single ($3\times10^{11}$ or $4\times10^{11}$) collection is entered at block 212, such as on touch sensitive field 109. Depending upon whether a double collection or triple collection has been selected, a number of platelets defining a double collection (or triple collection) is entered at block 214, such as on touch sensitive field 110. Lastly, a maximum procedure time is entered at block 216, such as on touch sensitive field 111.

Figure 3:
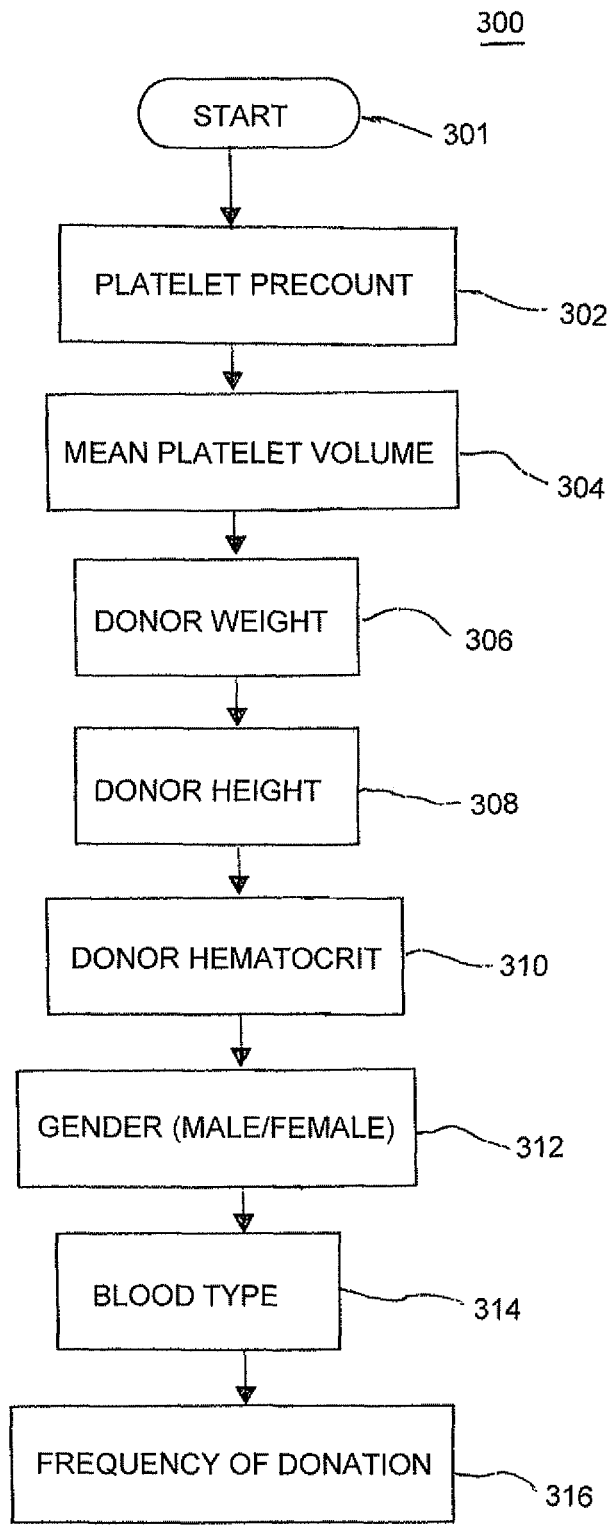
FIG. 3 is a flow diagram of information about a particular donor which may be entered prior to a blood component collection procedure, which the product options calculator will utilize in determining the blood products which may be collected from the particular donor.

FIG. 3 is a flow chart, generally designated 300, of information about a particular donor that can be entered prior to a blood component collection procedure, which the product options calculator will utilize in determining the blood products that can be collected from the particular donor. That is, product options calculator 120 can utilize specifically entered information in FIG. 3 rather than or in addition to corresponding preset information in FIG. 2 when determining the available blood component collection options.

At block 302 of FIG. 3, a platelet pre-count can be entered, such as at a keyboard of the apheresis instrument 100. At block 304, a mean platelet volume can be entered. At block 306, the donor's weight can be entered. At block 308, the donor's height can be entered. At block 310, the donor's hematocrit can be entered. At block 312, the donor's gender (male/female) can be entered. At block 314, the donor's blood type can be entered. Lastly, at block 316, the frequency of donation (frequent, infrequent, etc.) can be entered.

Once the presets of FIG. 2 and the specific information of FIG. 3 have been entered, the operator initiates the product options calculator 120, such as at a touch sensitive field 112 on the display 102. The product options calculator 120 then utilizes the default information and the entered information to determine all of the blood components which may be collected from the particular donor. The product options calculator 120 can also compare blood component collection options to limits set by industry standards and/or other rules such as platelet post count, post hematocrit, total volume of plasma to collect, and maximum volume of whole blood to process.

The product options calculator 120 can utilize a variety of processes and programming to determine available blood component collection options and to display the determined options on display 102.

Figure 4:
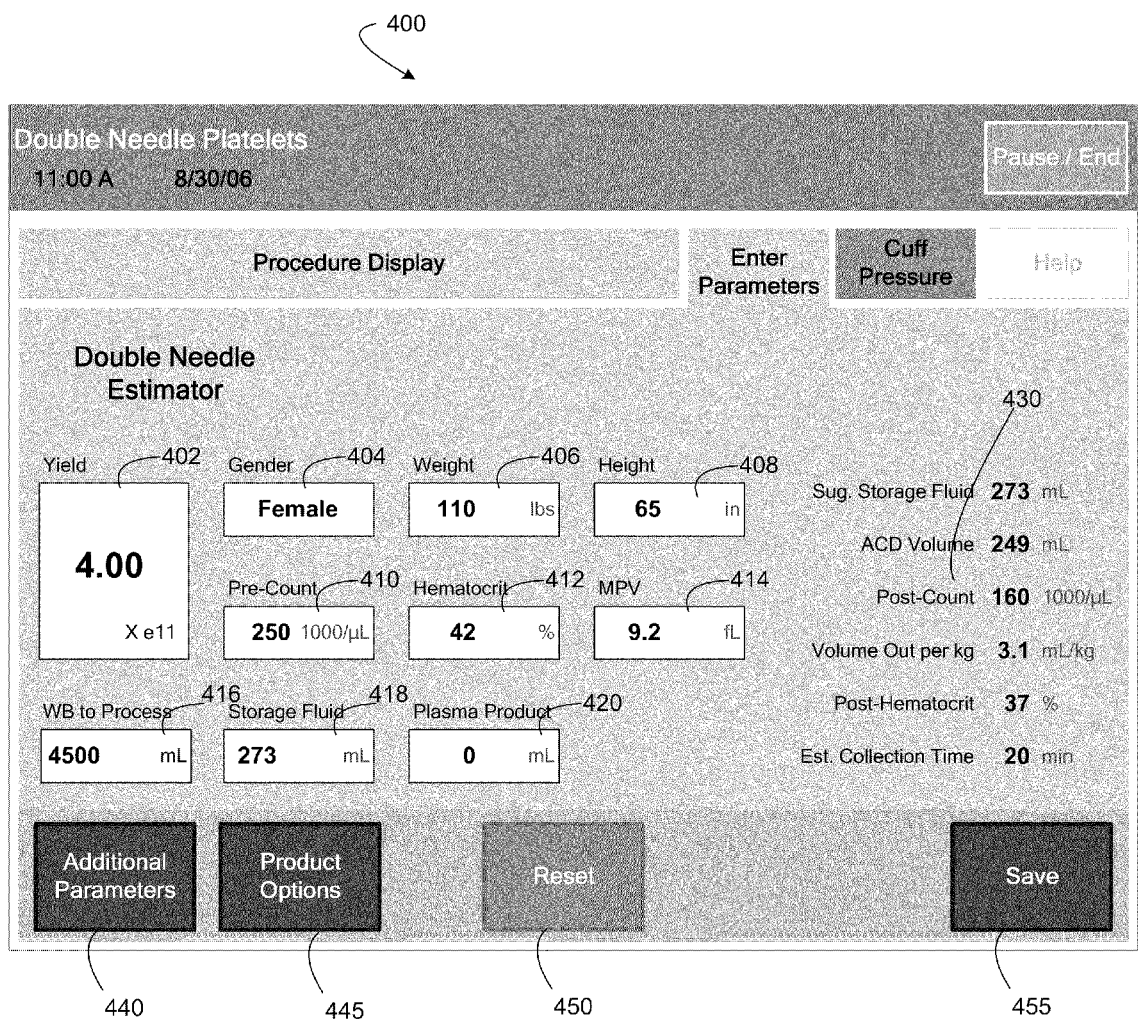
FIG. 4 is an example interface by which a user can enter parameter information for a double needle platelet procedure.

FIG. 4 shows an example estimator interface 400 by which a user can enter parameter information for a double needle platelet procedure. A similar interface and parameter settings can be provided for a single needle platelet procedure. As shown in FIG. 4, a user can enter and/or select parameter values such as an estimated yield 402 for a blood collection procedure, a donor gender 404, a donor weight, a donor height, a platelet pre-count 410, a donor hematocrit 412, a Mean Platelet Volume (MPV) 414, a whole blood (WB) to process 416, a storage fluid volume 418, and a desired plasma product 420. Entering parameter information via the interface 400 generates output information 430 for user review, such as a suggested storage fluid volume, estimated acid-citrate-dextrose (ACD) solution volume used, platelet post-count, blood volume out per kilogram, post-hematocrit, estimated collection time, etc. The interface 400 can also provide a user with options such as entry of additional parameters 440, calculation of product options 445, reset 450, saving values 455, etc. Parameter entry for product options determination can be one of a variety of functions and/or tabs offered by the interface 400.

For example, as shown in FIG. 4, a user can input a desired yield 402 of $4.00 \times 10^{11}$ or WB to process 416 of 4500 milliliters, along with a donor gender 404 of female, a donor weight 406 of 110 pounds, a donor height 408 of 65 inches, a platelet pre-count 410 of 250,000 platelets per microliter, an MPV 414 of 9.2 femtoliters, a storage fluid 418 of 273 milliliters, and a plasma product 420 of 0 milliliters. A double needle estimation 430 and a corresponding WB to process 416 or yield 402 can be determined including a suggested storage fluid volume of 273 milliliters, an estimated ACD volume used of 249 milliliters, an estimated post-count of 160,000 platelets per microliter, a volume out per kilogram of 3.1 milliliters per kilogram, a post-hematocrit of 37%, and an estimated collection time of 20 minutes.

Figure 5:
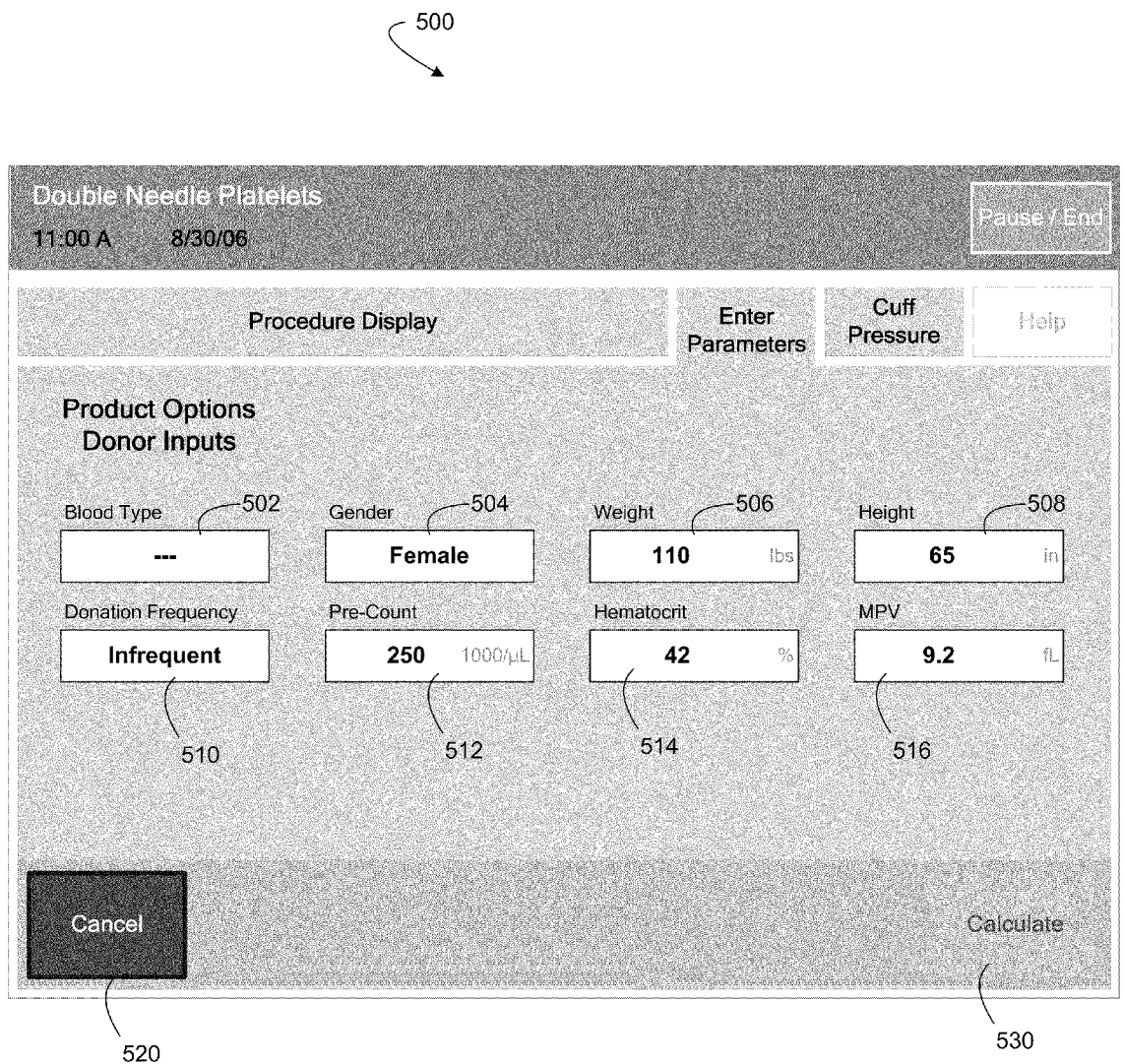
FIG. 5 is an example interface by which a user can enter additional donor input for product options.

FIG. 5 depicts an example interface 500 by which a user can enter additional donor input for product options. As shown, for example, in FIG. 5, additional donor options can include blood type 502, gender 504, weight 506, height 508, donation frequency 510, platelet pre-count 512, hematocrit 514, and/or MPV 516. The interface 500 can provide a user with buttons to cancel 520 input information and/or to calculate 530 donor product option(s), for example. One or more donor inputs can be automatically transferred from the estimator 400, for example. In certain examples, if a user changes values via the production options donor input interface 500, corresponding changes are made to the estimator interface 400 values.

Figure 6:
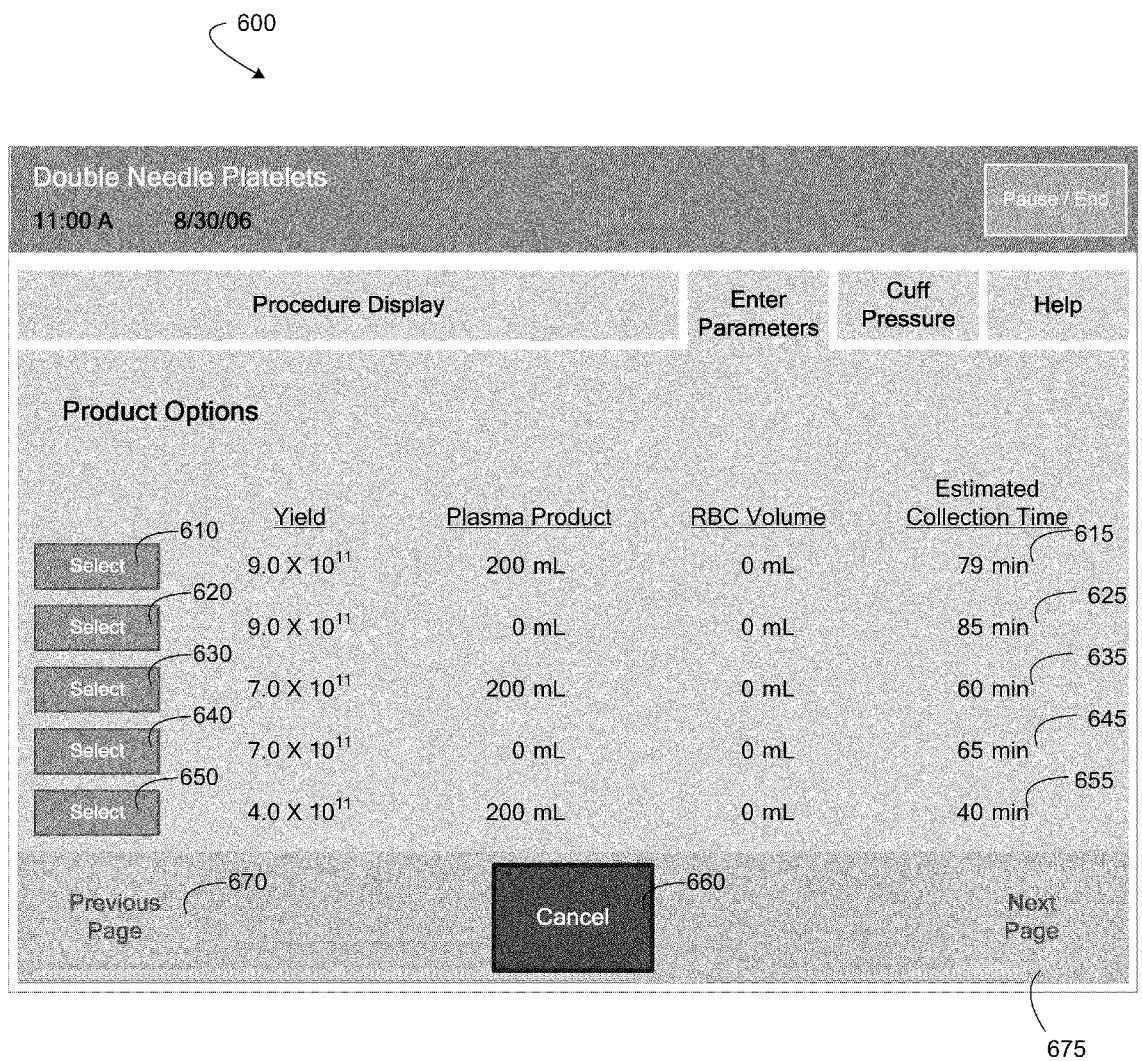
FIG. 6 is an example interface providing available product options for selection by a user.

FIG. 6 shows an example interface 600 providing available product options for selection by a user. As shown, for example, in FIG. 6, the interface 600 can provide one or more product options 610, 620, 630, 640, 650 for selection by a user. Each option can include information 615, 625, 635, 645, 655 related to the option 610, 620, 630, 640, 650 such as yield, plasma product, red blood cell (RBC) volume, and estimated collection time. A user can select an option 610, 620, 630, 640, 650 to provide configuration options for a blood collection and/or processing system. Configuration options can be used to automatically configure the system via a network and/or other data communication connection and/or can be used to guide an operator in manual configuration of the system, for example. The user can also navigate to different pages or screens of information 670, 675 via the interface 600 and/or cancel 660 activity, for example.

Once a user has input donor and/or other information as illustrated in FIGS. 4 and 5, for example, product options, such as product options shown in FIG. 6, can be determined based on available information. A product options calculator can be used to assist a blood center in selecting a procedure based on the blood center's requirements, preferences, rules, etc. Selection of an available blood product collection option via the interface 600 then populates blood processing system parameters based on the parameters for the selected option, for example.

Figure 7:
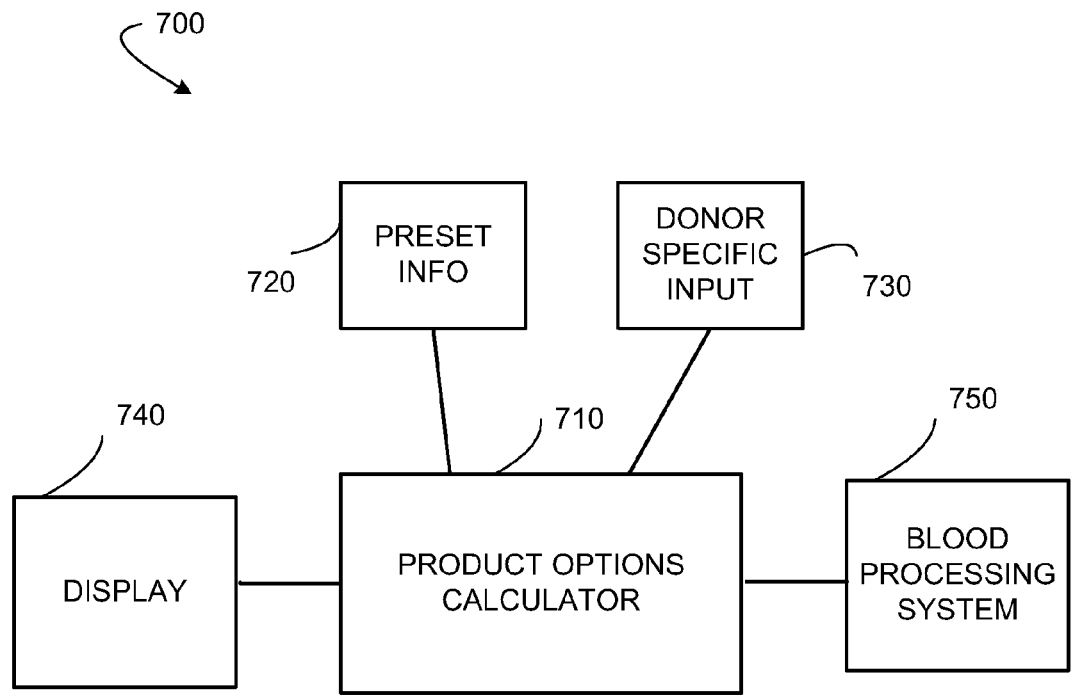
FIG. 7 illustrates an example product options calculator system providing available blood collection procedure(s) for operator review and configuration based on available input information.

FIG. 7 illustrates an example product options calculator system 700 providing available blood collection procedure(s) for operator review and configuration based on available input information. The system 700 includes a product options calculator 710, a preset information module 720, a donor-specific input module 730, a display 740, and a blood processing system 750. The components of the system 700 can be implemented alone and/or in various combinations of hardware, software, and/or firmware, for example. To the extent that the system 700 is implemented as software, one or more of the components of the system 700 is expressly defined to include machine readable instructions stored on a tangible medium. Any of the components of the system 700 as an Application Specific Integrated Circuit ("ASIC") and/or other logic circuit, for example.

The product options calculator 710 takes default and/or other preset information found in the preset information module 720 from a source such as a memory, a library, a database, etc., to establish an initial set of available blood collection and/or processing procedures. In addition to or in an alternative to manufacturer and/or supplier specific presets or defaults, a user can preselect and store values to be used as preset information in the event that donor-specific information is not available and/or provided, for example.

The donor-specific input module 730 includes is provided by a user and/or other data source (e.g., a memory, a library, a database, etc.) to modify, replace, and/or add to the preset information 710 for a particular donor. Based on the preset information 720 and the donor-specific input 730, the product options calculator 710 determines a list of available procedures and their associated parameters. This list or set of options is provided to a user for selection and/or further modification. The list can be provided by the product options calculator 710 to a user via the display 740. Upon user selection, parameters (and other configuration information) for a selected procedure are provided to the user via the display 740. In certain examples, the procedure information is provided to the blood processing system 750. In certain examples, the procedure information can also be transmitted to another system via a network, stored, and/or printed, for example.

Donor parameters can be input along with product options defaults in a user interface menu, such as a platelet yield estimator (PYE) defaults menu (or sub-menu). Once inputs are entered and Determine Product Options is selected (e.g., via button push or selection), product combinations that can be obtained from the donor are calculated. Procedure options can be limited by considerations of extracorporeal blood volume (ECV) limit (or equivalent intravascular deficit (IVD) limit), post hematocrit limit, platelet post-count limit, plasma volume out limit, and/or procedure time limits, for example. ECV/IVD (with ECV typically measured in percent and IVD typically measured in milliliters per kilogram) and time limits can be adjusted by the blood center, for example. Possible procedures are displayed in a list showing component product yields, volumes, and procedure time, for example. An operator can select a procedure from the list to reveal a complete list of estimated procedure data and transfer the parameters into the PYE, for example, from which the values may be modified prior to transfer to the platelet procedure. The performance and function of the PYE can remain unchanged for parameter setting without needing to rely on the product options calculator, for example.

In certain examples, default values can be set for a PYE. PYE default values can be changed via a menu displayed to a user and stored in memory, for example. In certain examples, upper and lower boundaries can be set for procedure parameters that cannot be exceeded by an operator inputting values. In certain examples, a last saved value stored for a parameter can be displayed for a user and can be either accepted or modified by the user. A user can restore factory and/or product options defaults upon selection of a button or option, for example. Example yield estimator defaults and product options defaults are shown in the tables below.

Figure 8:
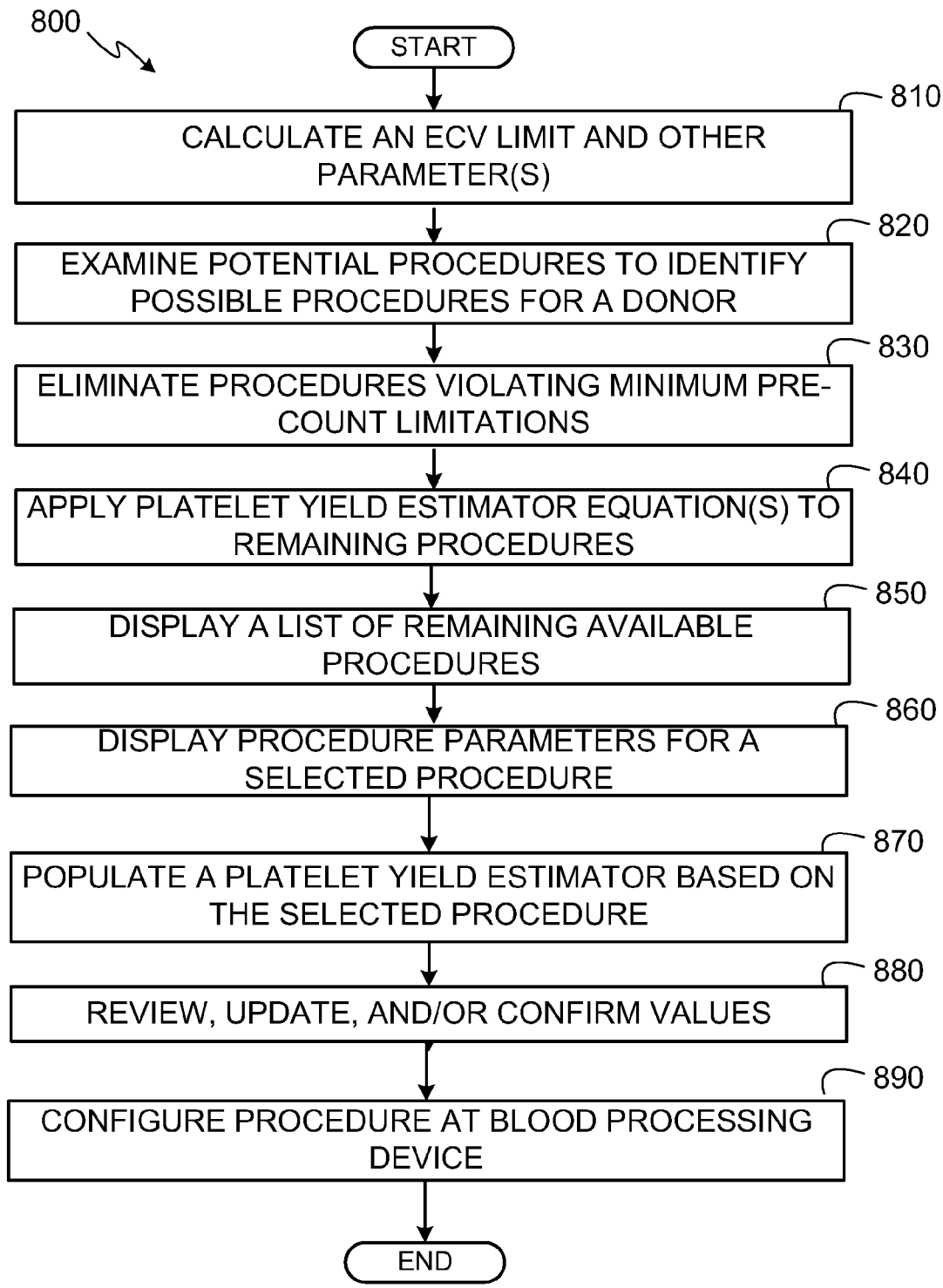
FIG. 8 is a flow diagram for an example product options calculator procedure.

In an example product options calculator procedure 800, shown in FIG. 8, an ECV or IVD limit and/or other parameter information is calculated at 810. For example, if the ECV limit is based on a percent, then the ECV limit is obtained from a product options default value. If the ECV limit is based on percent, then, for females, Total Blood Volume= $(0.3561*H^3+0.03308*W+0.1833)*1000$, where H represents donor height and W represents donor weight. For males, Total Blood Volume= $(0.3669*H^3+0.03219*W+0.6041)*1000$. The ECV limit can then be calculated as ECV Limit= $100*ecv\_limit*Total Blood Volume$. If the ECV limit is based on milliliters per kilogram (ml/kg), the ECV limit can then be calculated as ECV Limit= $10.5*donor weight$. As discussed above, a variety of default values can be provided and modified by a user to provide parameters for a particular donor and/or blood processing system configuration for use in identifying applicable blood/soft good product collection procedures.

For example, yield estimator defaults can include platelet pre-count; mean platelet volume; target platelet collection yield; single needle or double need adjustment; single, double, or triple dose storage fluid amount; double or triple dose limit; etc. Product options defaults can include, for example, ECV or IVD limit; RBC type; double or triple minimum pre-count; double or triple platelet yield, plasma product for procedure; maximum procedure time; etc. Other common procedure defaults can include, for example, ACD container weight; saline container weight; single, double, or triple dose whole blood volume limit; etc.

At 820, potential procedures are examined or "stepped through" to identify procedures possible for the given donor parameters. For example, several potential procedures are shown in the table below.

| Procedure | Platelet Yield | RBC Volume | Plasma Volume |
|---|---|---|---|
| 1 | Triple Yield | Max RBC Volume | Plasma Product |
| 2 | Triple Yield | Max RBC Volume | 0 |
| 3 | Triple Yield | 0 | Plasma Product |
| 4 | Triple Yield | 0 | 0 |
| 5 | Double Yield | Max RBC Volume | Plasma Product |
| 6 | Double Yield | Max RBC Volume | 0 |
| 7 | Double Yield | 0 | Plasma Product |
| 8 | Double Yield | 0 | 0 |
| 9 | Single Yield | Max RBC Volume | Plasma Product |
| 10 | Single Yield | Max RBC Volume | 0 |
| 11 | Single Yield | 0 | Plasma Product |
| 12 | Single Yield | 0 | 0 |

At 830, for each combination of products, product collection procedures are eliminated that violate minimum pre-count limitations. The following provide several illustrative but non-exclusive examples of limitations/guidelines examined to remove collection procedures from an available list of procedures for a particular donor.

For example, if a platelet pre-count is less than a triple minimum, then the donor's pre-count is too low for a triple platelet product. If the platelet pre-count is lower than a double minimum, then the donor's pre-count is too low for a double platelet product. If an operator has selected a single needle platelet estimator and a maximum RBC volume is zero, then RBC volume is set to zero in procedure defaults, and procedures relying on a maximum RBC volume are removed from the set of available procedure options. Depending upon donation frequency, procedures with a non-zero RBC volume may be removed from the available options because the donor's donation frequency does not allow collection of an RBC product. If a plasma product is zero, then procedures involving a plasma product volume are removed from the available options and plasma product is set to zero in procedure defaults. Additionally, a plasma product can be set to zero for a female donor, regardless of other characteristics. If the operator has selected a double needle platelet estimator, then procedures with a non-zero RBC volume are removed from the available list for the donor. If the donor's blood type (e.g., A+, A−, B+, B−, AB+, AB−, O+, O−) is not one defined in requested RBC types, then procedures with a non-zero RBC volume are removed from the available list of procedures because the donor blood type does not match requested RBC type(s). If the donor's plasma type is not found in requested plasma types, then procedures with a non-zero plasma product are removed from the list of available procedures.

At 840, platelet yield estimator equation(s) are applied to each remaining procedure in the list of available procedures. For example, if a donor's weight is less than a low weight limit, then procedures with an absolute plasma volume of greater than a low weight plasma limit are removed from the available procedure list. Procedures with an absolute plasma value greater than a high weight plasma limit are removed from the available procedure list. If a donor's platelet post-count is less than a post-count limit, then the affected procedure is removed from the list. For example, if the procedure calls for a triple platelet yield, then the procedure is removed because the donor's post-count does not allow a triple platelet product. For example, if the procedure calls for a double yield, then the procedure is removed because the donor's post-count does not allow a double platelet product. Procedures in which the percentage of blood out is greater than the ECV/IVD limit and procedures having an estimated collection time greater than a maximum procedure time can also be removed from the list of available procedures.

At 850, a list of remaining procedures is displayed. Procedure information displayed can include platelet yield, plasma product, RBC volume, procedure time, etc. associated with a procedure option. If no procedures satisfy the examined criteria, then no procedures are listed and displayed for the user. If all procedures examined have a percentage out that exceeds the set ECV limit and/or a minimum estimated collection time that exceeds the set maximum procedure time, then an appropriate alarm (e.g., "Max ECV Limit Exceeded" and/or "Max Procedure Time Limit Exceeded") can be displayed to the user.

At 860, when a user selects a procedure from the available list, procedure parameters are displayed to the user. For example, procedure parameters are provided in the table below.

| Parameter | Units |
| --- | --- |
| Yield | x e+11 |
| Plasma Product/Storage Fluid | ml |
| RBC Volume | ml |
| WB to Process | ml |
| ACD Volume | ml |
| Post-Count | 1000/µl |
| Total Volume Out | % |
| Volume Out per Kilogram | ml/kg |
| Post-hematocrit | % |
| Estimated Collection Time | minutes |

At 870, a user can populate the platelet yield estimator based on the selected procedure. The data fields of the platelet yield estimator are then populated with the selected procedure parameters. In certain examples, parameters can be transferred if a procedure is currently running. Some or all of the parameters and their values are transferred to the selected procedure and may be displayed to the user.

At 880, the user can review, update, and/or confirm parameter and/or other configuration values. The user can reset values to original defaults, for example. At 890, the procedure is configured at the blood collection device.

Certain examples can be used in conjunction with one or more blood collection and/or processing devices and can be incorporated into a network of data communication and information exchange between a blood center, blood component collection instruments, and the like. For example, certain examples provide systems, apparatus, and/or methods for collecting, using, and storing information in a biological fluid collection and/or processing facility. Certain examples can be incorporated into an existing facility's system via an upgrade to existing hardware and software. Certain examples provide a data connection between laboratory instruments, including, but not limited to, existing blood and blood component collection instruments, such as the Autopheresis-C, ALYX, and/or AMICUS instruments which are supplied by Fenwal, Inc., such as those systems described in PCT Publication No. WO 01/17584, U.S. Pat. Nos. 5,581,687 and 5,956,023, and U.S. Ser. No. 09/037,356, and biological treatment instruments, such as the pathogen inactivation instruments described in U.S. Ser. No. 09/325,599, which are incorporated by reference herein, and the collection facility's management information system which lends itself to automated tracing and/or tracking of donors and biological fluids data logging. Traceability can be provided via integration of donor, operator, soft goods, and instrument data. In certain examples, event reporting can be automated for regulatory compliance.

In certain examples, the system is designed for a biological fluid collection and/or processing facility as an accessory to the instruments used in those facilities. The general purpose of the system is to increase the efficiency of processing biological fluids and aid in the regulatory compliance process. This purpose is fulfilled principally through the collection of more information and more accurate information. Currently, facility staff must manually keep track of information such as by writing information on a clipboard, but the present system allows the staff and operators to skip the paper/manual steps. The system may also provide some of the following benefits: more accuracy and completeness in the data that is already being collected manually; more data collected for diagnostic use, which may give rise to better information with which to design or troubleshoot laboratory instruments; more data collected for use by the center for generation of ad-hoc statistical reports, which could relate any number of variables such as donors per day/per time of day, rate of errors, collection amount by type of donor, etc.; more data collected for use by the center to determine the efficiency and error rate of different operators, which in turn can inform decisions to institute better training or could substantiate a complaint against a facility operator; greater efficiency on the floor, due to less paperwork; lower costs due to less office paperwork; ability to research all the detailed information on a single procedure, or on the history of a single donor, as a way to find information pertaining to a donor complaint, or something wrong with the product, or any other complaint or error; more complete records and statistical and trend reports to help ease compliance reviews; accurate monitoring of the facility procedures; collection of information that may help the facility's staff improve their efficiency/workflow.

In certain examples, the instruments, laboratory equipment, as well as data input devices are connected to an Ethernet along with other data processing applications. Certain examples are also suited for connecting legacy instruments that automatically transmit or can be configured to periodically transmit data via a serial or parallel interface and protocol converters. A computer acting as a server/gateway runs applications to receive the transmitted data and route them to database and hypertext markup language (HTML) applications. Each data packet bears a unique identifier which identifies the source of the data.

In certain examples, users can perform data query and reporting on a local area network, through a wide area network, over the Internet, or a combination of two or more of these, using a standard browser application interface. Real-time viewing and updating of device operation can be configured for any number of devices on the browser. In addition, the server also presents abbreviated data to a wireless personal digital assistant (PDA) also running a standard application browser interface for portable information and viewing and alarm and event notification. The PDAs are also used for data input (through a keypad touch screen, scanning, or other entering method—all used interchangeably herein) in association with an apparatus operation. Thus, certain examples include an open standard architecture in a heterogeneous apparatus environment with real-time update and access of data, and portable data viewing, reporting, notification, and inputting.

Figure 9:
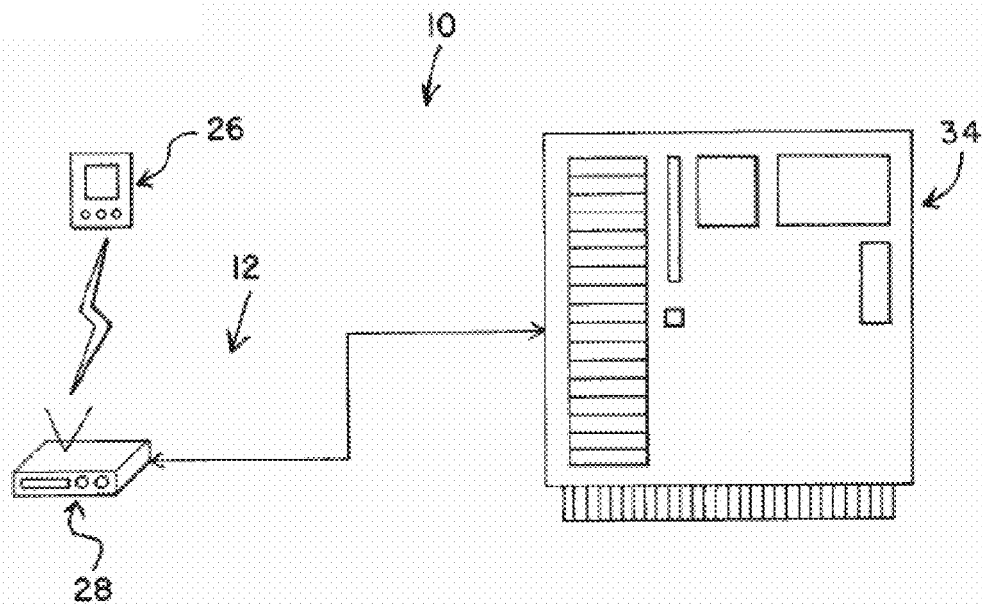
FIGS. 9 through 12 provide example networked systems that can be used in conjunction with the product options calculator and blood processing systems described herein.

In certain examples, the product options calculator described above can be included in and/or operate in conjunction with a data communication network. Referring to FIG. 9, for example, the system/apparatus 10 includes a first network 12 comprising a system server 34 including a memory, a communication driver and an HTML application capable of running embedded javascript code and at least one wireless data interface, such as a PDA and/or scanner 26. In certain examples, the at least one wireless data interface includes enough PDAs and scanners to accommodate several facility operators and/or donors at a time and a wireless access point 28.

Figure 10:
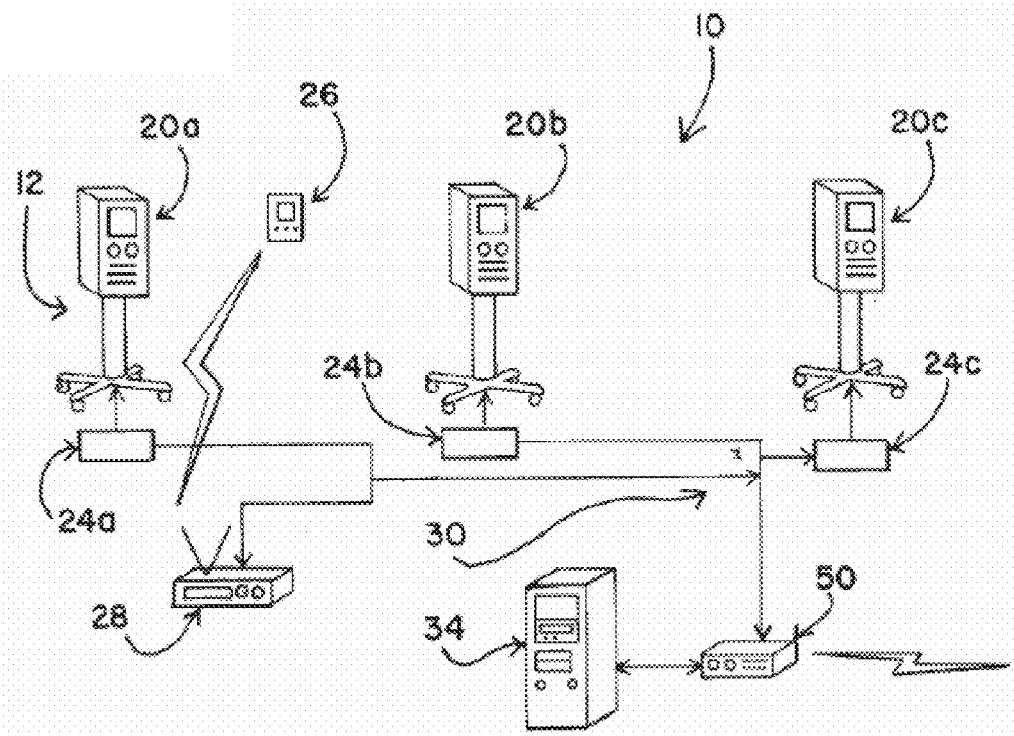

In a second embodiment illustrated in FIG. 10, the apparatus 10 includes hardware and software component parts and provides for inter-process communication. FIG. 10 shows a first network 12. The first network 12 includes laboratory instruments 20a, 20b, 20c, serial/parallel to Ethernet converters 24a, 24b, 24c, such as a PicoWeb™ device by Lightner Engineering located in San Diego, Calif. or a NetDev™ device by Fenwal Inc., where needed, a first Ethernet 30, and a system server 34 including a memory, a communication driver for the apheresis instruments, a communication protocol converter, and an HTML application with embedded javascript code.

The first network 12 can communicate via the Internet through a network switch 50. The network switch 50, which can be incorporated within the system server 34, includes a processor which allows the switch to distinguish the sources of the information which it receives.

Figure 11:
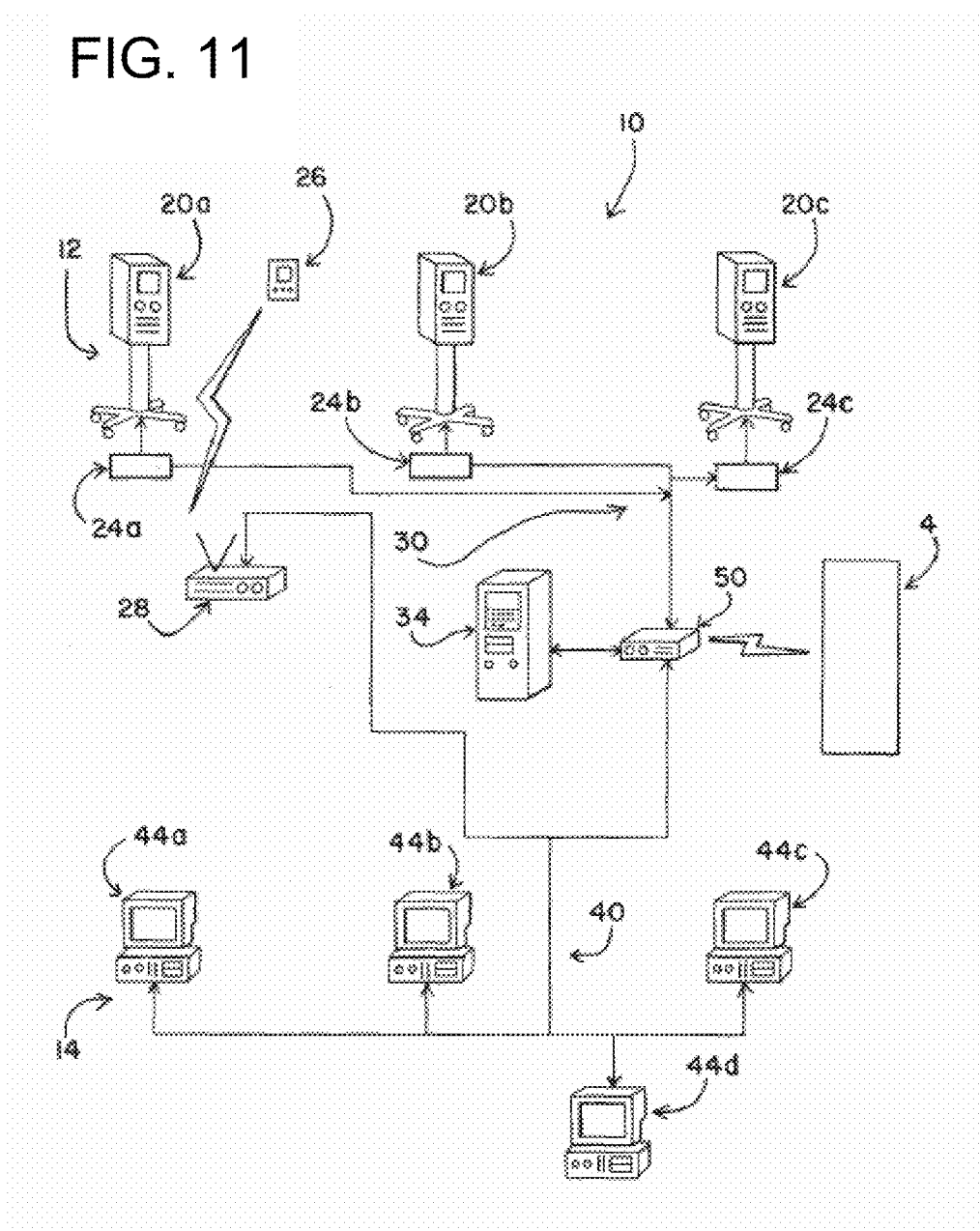

FIG. 11 shows a pair of networks 12, 14. The network switch 50 provides the communication link between the networks 12, 14. Again, the network switch 50 includes a processor which allows the switch to distinguish the sources of the information which it receives. The first network 12 includes laboratory instruments 20a, 20b, 20c, serial/parallel to Ethernet converters 24a, 24b, 24c where needed, a first Ethernet 30, and a system server 34 including a memory, a communication driver for the instruments, a communication protocol converter, and an HTML application capable of running embedded javascript code.

The second network 14 includes a second Ethernet 40 and data interfaces 44a, 44b, 44c, 44d, e.g. personal computers to run server and browser software. At least one of the data interfaces 44a, 44b, 44c is equipped with a barcode scanner for setting up facility operators and associating them with preprinted badges. The second network 14 also includes at least one wireless data interface, preferably a PDA and/or scanner 26, but more preferably enough PDAs and scanners to accommodate several facility operators and/or donors at a time and a wireless access point 28.

A central server 48, generally located at a remote site, may communicate with the first and second networks 12, 14 via the Internet using a communication link such as a modem, digital subscriber line, or the like with the network switch 50. The central server 48, therefore, can access data regarding the instruments 20a, 20b, 20c that are stored in the system server 34.

The first network 12 is primarily established between the system server 34 and the instruments 20a, 20b, 20c. This first network 12 is not directly connected to the Internet or any other subnetwork except through the network switch 50. The network switch 50 is adapted to prevent unwanted communication with external servers and/or other means of data communication while at the same time being configured to forward useable Ethernet datagrams broadcast packets ("UDP") to all ports.

The system server 34 controls the distribution of data throughout the system 10. The system server 34 runs an operating system, such as a Linux machine running SuSE 6.4 or more preferably a personal computer running Microsoft 2000. The system server 34 receives data from an instrument 20a via one of the serial/parallel to Ethernet converters 24a and/or other interfaces within the apparatus 10. Accordingly, the system server 34 includes one or more Ethernet cards to connect sets of apheresis instruments 20a, 20b, 20c to the system server 34 and at least one additional Ethernet card to connect the system server 34 to the facility's office network which is also connected to the central server 48. The system server 34 also runs a web server, such as Apache or more preferably Microsoft Internet Information Server provided with Microsoft 2000.

Each instrument 20a, 20b, 20c connected to the apparatus 10 is identified by a unique number such as an internet protocol ("IP") address and a serial number. Certain legacy instruments provide framing bytes on data packets coming through a parallel port. The serial/parallel to Ethernet converters 24a, 24b, 24c gather data from the instruments 20a, 20b, 20c and deliver the data into an Ethernet frame buffer. The data is transmitted via the first Ethernet 30 to the system server 34. Server software takes the data and outputs web pages of information. It should be noted that the Ethernet converters 24a, 24b, 24c are necessary for certain legacy devices and may not be needed in every application of the present system 10.

Figure 12:
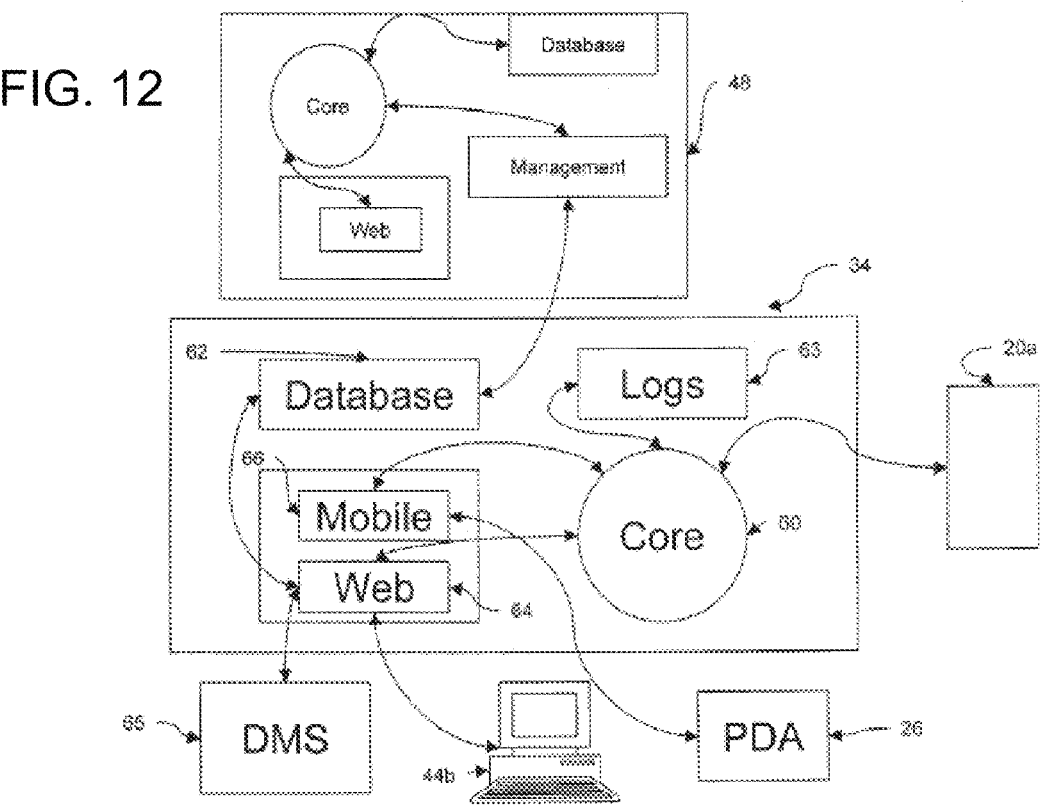

Referring to FIG. 12, the instrument 20a is the primary source of data for the system 10. The instrument 20a may provide parallel data packets to the serial/parallel to Ethernet converter 24a which converts the packets to useable Ethernet datagrams (user datagram protocol/internet protocol ("UDP/IP") packets). The first Ethernet 30 transmits the UDP data packets to the system server 34.

The software within the system server 34 performs two separate functions. The first function gathers data from the instruments 20a, 20b, 20c. This function receives the UDP packets from the first Ethernet 30. The second function outputs HTML files to web clients by sending and receiving remote method invocation ("RMI") data. Accordingly, the server software includes separate modules for performing these functions.

Still referring to FIG. 12, a core module 60, including a java program, communicates with the first Ethernet 30 and also communicates with the other modules within the system server 34. The core module 60 handles access with a database module 62 and caches information from the instrument 20a that is monitored on a frequent basis via data interface 44b and/or the PDAs 26. The core module 60 also writes to a high resolution log filing system 63 and performs the bulk of the business logic.

First, the core module 60 receives UDP packets from one of the instruments 20a and tracks the instrument's process. A converter network protocol module includes a protocol describing network communications between the instruments 20a, 20b, 20c and the system server 34 and a converter boot procedure used in conjunction with a bootp server which contains the IP addresses for the instruments 20a, 20b, 20c. The bootp server contains the Internet protocol that enables a diskless workstation to discover its own IP address, the IP address of a bootp server on the network, and a file to be loaded into memory to boot the machine. This enables the workstation to boot without requiring a hard or floppy disk drive. The converter network protocol and the converter boot procedure modules are specifications and not software.

The data transferred from the instruments 20a, 20b, 20c to the core module 60 can be used to create HTML web pages for monitoring the instruments via a structured query language (SQL) open database connectivity interface (ODBC). The core module 60 writes to the database module 62, which includes a SQL database server, to save and manage the instrument data. Javascript is used to create database tables on the SQL server and creates definitions for each table and field. The SQL database server stores all apparatus data except for high resolution logs.

The SQL database server preferably uses MySQL and more preferably Microsoft SQL Server. The SQL database server saves the data into a disk array. Java code within the HTML files provides a SQL interface to the SQL database server 62.

A web module 64, comprising the web server, can access the SQL database server using the ODBC interface. The web module 64 serves the web pages on the second Ethernet 40 so that the instruments 20*a*, 20*b*, 20*c* on the first Ethernet 30 are not interfered. The second Ethernet 40 allows standards such as javascript and hypertext preprocessor (PHP) codes to be viewed. The javascripts and/or PHP can be used to query and search the database.

The web module 64 communicates with the core module 60 via RMI data transmission. The core module 60 sends RMI data to the web module 64. Hypertext transfer protocol (HTTP) data generated by the web module 64 are served to and received from the web browser 44*b* via the web module 64 and the second Ethernet 40. The web browser 44*b* can act as a central workstation for monitoring the workflow within the blood collection facility. HTTP data can further be served to and received from the facility's donor management system ("DMS") 65.

A mobile module 66 controls the system server's 34 communications with the PDAs/scanners 26. Thus, PDAs/scanners 26, such as the Palm Pilot™ by Symbol, are also a source of data to the system server 34. Preferably, each PDA/scanner 26 includes a wireless RF link and a built-in bar code scanner. The wireless feature of the PDA/scanner 26 allows the users to move freely in a room such as a blood center and scan barcoded material knowing it was logged into the database. The human error from manually writing down a number onto a log sheet is, thus, eliminated.

The core module 60 communicates with the PDAs/scanners 26 via the mobile module 66 by transmitting and receiving RMI data to and from the mobile module 66. The core module 60 can also serve data regarding the instruments 20*a*, 20*b*, 20*c*, such as an instrument's screen display or status, to a PDA/scanner 26 in real time or near real time. Thus, the wireless access point 28 provides the link between the system server 34 and the PDAs/scanners 26.

The mobile module 66 communicates HTTP data to and from the PDAs/scanners. The PDA/scanner 26 can be used to scan the barcodes of plastic disposable kits, bleed numbers, donor ID cards, operator ID cards, and the instrument itself, and transfer that information to the core module 60 via the mobile module 66. Data that was historically manually recorded at blood centers can now be barcoded and logged electronically and wirelessly via the PDA/scanner 26. Date and time are automatically logged with such information.

Finally, a downtime module contains a java program that performs downtime tasks, including software updates.

The central server 48 is generally located at a remote site and preferably runs a Windows 2000 operating system. The central server 48 is also referred to as a headquarters (HQ) server. The central server 48 is connected to facility networks through an IP network and is, therefore, necessarily more powerful than the facilities' system servers 34 due to the larger database size. The central server 48 must be capable of contacting any remote server at any time. There is not a wireless base station 28 or instrument 20*a*, 20*b*, 20*c* at the HQ level. Personal computers at the headquarters office connect to the central server 48 through HQ office network (IP). Personal computers at the facilities may also connect to the central server 48. Other computer devices with a browser interface and internet/networking capability can also connect to the server with proper security passwords and/or identification.

Similar to the system server 34, the central server 48 includes modules that perform predetermined functions, including a central core module 70, a central database module 70, and a central web module 72. In addition, the central server contains a central management module 74, a database connect file, and an installation procedure.

The central management module 74 is an interactive java program used by HQ management to perform continuous backups and software updates while the database connect file is a file containing the password for the SQL server database. The installation procedure is a procedure for installing server networking and files necessary to start the initial facility network upgrade process, including a setup program.

The central database module 74 houses a database composed of all the facilities' databases merged together. The central database module 74 is designed to facilitate the database merge by insuring that the definitions of unique keys do not conflict. All data is collected by and lives in the facilities' database modules 64. There can be many such facility database modules 64 in communication with the central server 48. The system servers 34 are the servers for all communications with the donor management systems 65.

Optionally, a company operating several facilities, each having its own system server 34, may also have a dedicated central database. This dedicated central database is equivalent to the database module 64 except: (1) many of the functions of the database module 64 cannot be used because the central server 48 is not connected to any wireless devices or apheresis instruments; and (2) an additional program is needed to run the dedicated central database with the contents of the several system databases. This synchronization program communicates directly with the system servers and updates any changes from the system server 34 to the central server 48.

In use, the facilities provide inputs to the system server 34 through an HTTP call for each procedure which is initiated from their donor management system before the system server will store data for the procedure. The facilities may issue HTTP requests for data from their system servers 34 for limited bleed summary fields, using a programmatic interface, in addition to the HTTP browser-based reporting interface from the central server 48.

The apparatus 10 may be called a "distributed system;" however, the system server 34 operates independently as if it were not part of a distributed system. The central or HQ server 48 takes initiative to copy data in both directions as needed.

The system server 34 always operates in server-mode with respect to communications with headquarters and other systems, and never operates in client-mode. The donor management system and the central server 48 operate in client-mode. In server mode, the system server 34 waits for requests and does not initiate transactions with other servers. This achieves the benefits of centralizing data management functions (like backups) while retaining the robustness of independent servers.

Thus, certain examples provide a listing of all available blood components that can be collected from a particular donor. Certain examples display a list of the available blood component products that can be collected from a particular donor, including estimated component product yields, volumes, and procedure time, for example. Certain examples help simplify and avoid errors in the selection of the type of blood component to be collected from any particular donor.

While particular embodiments of the invention have been shown and described, it will be obvious to those skilled in the art that changes and modifications may be made therein without departing from the invention in its broader aspects.

It will be appreciated by persons skilled in the art that numerous variations and/or modifications may be made to the invention as shown in the specific embodiments and/or aspects without departing from the spirit or scope of the invention as broadly described. The present embodiments and aspects are, therefore, to be considered in all respects as illustrative and not restrictive. Several embodiments are described above with reference to the drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any electronic device and/or machine-readable media suitable for accomplishing its operations. Certain embodiments of the present invention may be implemented using an existing computer processor and/or by a special purpose computer processor incorporated for this or another purpose or by a hardwired system, for example.

Embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

The invention claimed is:

1. A product options calculator system for an apheresis instrument, the product options calculator system comprising:
    a processor configured to implement:
    a preset information module to include preset information regarding blood component products and configuration information;
    a donor specific input module to receive donor specific information about a blood donor from a user as a plurality of donor parameters;
    a platelet yield estimator to apply the plurality of donor parameters to estimate a length of time to collect a desired yield for a blood component collection procedure;
    a blood product options calculator to calculate one or more available blood component collection procedure options, the options including at least one platelet collection procedure, and associated settings within the constraints of the preset information and the donor specific information from which a user can choose to configure the apheresis instrument,
        wherein the blood product options calculator is to calculate one or more minimum pre-count limits including calculating an extracorporeal blood volume (ECV) limit based on the plurality of donor parameters,
        wherein the blood product options calculator is to iteratively calculate the one or more available blood component collection procedure options that do not violate a set of one or more preset collection rules based on parameter information, the minimum pre-count limits, and estimated yield, and
        wherein the blood product options calculator is to compare a) the one or more available blood component collection procedure options to b) one or more preferences for collection with respect to a blood collection center included in the preset information to c) determine which of the one or more available blood component collection procedure options comply with the one or more preferences;
    a display for displaying available blood component collection procedure options to the user with respect to the apheresis instrument; and
    an interface to accept user input to select an available blood component collection procedure option displayed on the display, the interface to concurrently present at least one procedure parameter for each of the available blood collection procedure options via the display, the interface to provide the platelet yield estimator to the user and to launch the blood product options calculator from the platelet yield estimator via the displayed interface,
        wherein the platelet yield estimator is to provide an initial time and yield estimate based on each available blood component collection procedure option identified by the donor specific information and wherein selection of an available procedure option automatically populates the platelet yield estimator from the blood product options calculator and settings for the selected procedure option, and wherein the interface is to accept user input to review, update, and confirm settings for a selection blood component collection procedure option.

2. A product options calculator system in accordance with claim 1, wherein the preset information is selected from the group consisting of desired red blood cell type, desired plasma type, extracorporeal volume limit, minimum acceptable pre-count for a double platelet product, minimum acceptable pre-count for a triple platelet product, number of platelets that define a single collection, number of platelets that define a double or a triple collection, and maximum procedure time.

3. A product options calculator system in accordance with claim 1, wherein the donor specific information is selected from the group consisting of platelet pre-count, mean platelet volume, donor weight, donor height, donor hematocrit, gender, blood type, and frequency of donation.

4. A product options calculator system in accordance with claim 1, wherein the interface provides alerts to a user if information input by a user with respect to donor specific information exceeds a preset limit set for the product options calculator system.

5. A product options calculator system in accordance with claim 1, wherein the preset information is used by the product options calculator if donor specific information is not entered prior to a collection procedure using the apheresis instrument.

6. A product options calculator system in accordance with claim 1, wherein the blood product options calculator configures the apheresis instrument for a selection blood component collection procedure option.

7. A product options calculator system in accordance with claim 1, wherein the product options calculator system is connected to a network and transmits information related to a selected blood component collection procedure option via the network.

8. The product options calculator system in accordance with claim 7, wherein the network provides a data connection between laboratory instruments.

9. The product options calculator system in accordance with claim 7, wherein the network comprises an information exchange between biological fluid collection and processing facilities.

10. The product options calculator system in accordance with claim 1, wherein the blood products options calculator is to iteratively calculate the one or more available blood component collection procedure options by:
   removing the one or more available blood component collection procedure options based on the one or more minimum pre-count limits to obtain a first list of available blood component collection procedure options;
   calculating the one or more available blood component collection procedure options that do not violate the set of one or more preset collection rules based on the parameter information and the estimated yield to obtain a second list of available blood component collection procedure options;
   comparing the one or more available blood component collection procedure options of the second list to b) the one or more preferences for collection with respect to a blood collection center included in the preset information to c) determine which of the one or more available blood component collection procedure options of the second list comply with the one or more preferences; and
   removing the blood component collection procedure options from the second list that do not comply with one or more preferences from the available blood component collection procedure options.

11. The product options calculator system in accordance with claim 10, wherein the interface is to concurrently present the at least one procedure parameter for each of the available blood collection procedure options of the second list via the display.

12. The products options calculator system in accordance with claim 1, wherein the at least one procedure parameter for each of the available blood collection procedure options is one or more of a platelet yield count, a plasma product count, a red blood cell volume, a whole blood to process value, an acid-citrate-dextrose (ACD) solution volume, a platelet post-count value, a blood volume out per kilogram value, a post-hematocrit value, or an estimated collection time.

13. A method for calculating all of the blood component collection options for a specific donor, said method comprising:
   storing preset information regarding blood component products and apheresis configuration information;
   receiving donor specific information about a donor as a plurality of donor parameters;
   calculating an initial time and yield estimate for each available blood component collection procedure option identified by the plurality of donor parameters via a platelet yield estimator, the platelet yield estimator to launch a product options calculator;
   calculating one or more minimum pre-count limits including calculating an extracorporeal blood volume (ECV) limit based on the plurality of donor parameters;
   calculating, via the product options calculator, one or more available blood component collection procedure options and associated settings within the constraints of the preset information and the donor specific information from which a user can choose to configure the apheresis instrument, the options including at least one platelet collection procedure,
   wherein calculating comprises:
      iteratively calculating the one or more available blood component collection procedure options that do not violate a set of one or more preset collection rules based on parameter information, the minimum pre-count limits, and estimated yield, and
      comparing a) the one or more available blood component collection procedure options to b) one or more preferences for collection with respect to a blood collection center included in the preset information to c) determine which of the one or more available blood component collection procedure options comply with the one or more preferences;
   displaying the available blood component collection procedure options for user review and selection to configure a blood processing system, the displaying including concurrently displaying at least one procedure parameter for each of the available blood collection procedure options, and selection including to select an available blood component collection procedure option displayed on the display, wherein selection of an available procedure option automatically populates the platelet yield estimator from the product options calculator and settings for the selected procedure option;
   providing, via an interface, the platelet yield estimator to the user and launching the blood product options calculator from the platelet yield estimator via the interface; and
   accepting user input to review, update, and confirm settings for a selection blood component collection procedure option.

14. A method in accordance with claim 13, wherein the preset information is selected from the group consisting of desired red blood cell type, desired plasma type, extracorporeal volume limit, minimum acceptable pre-count for a double platelet product, minimum acceptable pre-count for a triple platelet product, number of platelets that define a single collection, number of platelets that define a double or a triple collection, and maximum procedure time.

15. A method in accordance with claim 13, wherein the donor specific information is selected from the group consisting of platelet pre-count, mean platelet volume, donor weight, donor height, donor hematocrit, gender, blood type, and frequency of donation.

16. A method in accordance with claim 13, wherein the preset information is used by the product options calculator if donor specific information is not entered prior to a collection procedure using the apheresis instrument.

17. A method in accordance with claim 13, further comprising configuring the apheresis instrument for a selection blood component collection procedure option.

18. A non-transitory computer readable storage medium having set of instructions for execution on a computing device, the set of instructions providing a blood product options calculator system when executed, the set of instructions comprising:
  a preset information module including preset information regarding blood component products and configuration information;
  a donor specific input module receiving donor specific information about a blood donor from a user as a plurality of donor parameters;
  a platelet yield estimator to apply the plurality of donor parameters to estimate a length of time to collect a desired yield for a blood component collection procedure;
  a blood product options calculator calculating one or more available blood component collection procedure options, the options including at least one platelet collection procedure, and associated settings within the constraints of the preset information and the donor specific information from which a user can choose to configure the apheresis instrument,
    wherein the blood product options calculator is to calculate one or more minimum pre-count limits including calculating an extracorporeal blood volume (ECV) limit based on the plurality of donor parameters,
    wherein the blood product options calculator is to calculate the one or more available blood component collection procedure options that do not violate a set of one or more preset collection rules based on parameter information, the minimum pre-count limits, and estimated yield, and
    wherein the blood product options calculator is to compare a) the one or more available blood component collection procedure options to b) one or more preferences for collection with respect to a blood collection center included in the preset information to c) determine which of the one or more available blood component collection procedure options comply with the one or more preferences;
  a display for displaying available blood component collection procedure options from the second list to the user with respect to the apheresis instrument; and
  an interface accepting user input to select an available blood component collection procedure option displayed on the display, the interface to concurrently present at least one procedure parameter for each of the available blood collection procedure options via the display, the interface to provide the platelet yield estimator to the user and to launch the blood product options calculator from the platelet yield estimator via the displayed interface,
    wherein the platelet yield estimator is to provide an initial time and yield estimate based on each available blood component collection procedure option identified by the donor specific information and wherein selection of an available procedure option automatically populates the platelet yield estimator from the blood product options calculator and settings for the selected procedure option, and wherein the interface is to accept user input to review, update, and confirm settings for a selection blood component collection procedure option.

19. A non-transitory computer readable medium in accordance with claim 18, wherein the preset information is selected from the group consisting of desired red blood cell type, desired plasma type, extracorporeal volume limit, minimum acceptable pre-count for a double platelet product, minimum acceptable pre-count for a triple platelet product, number of platelets that define a single collection, number of platelets that define a double or a triple collection, and maximum procedure time.

20. A non-transitory computer readable medium in accordance with claim 18, wherein the donor specific information is selected from the group consisting of platelet pre-count, mean platelet volume, donor weight, donor height, donor hematocrit, gender, blood type, and frequency of donation.

21. A non-transitory computer readable medium in accordance with claim 18, wherein the preset information is used by the product options calculator if donor specific information is not entered prior to a collection procedure using the apheresis instrument.

* * * * *